United States Patent [19]

Aspisi et al.

[11] 4,436,919
[45] Mar. 13, 1984

[54] BORANE COMPLEXES

[75] Inventors: Christian Aspisi, Boulbon; Marc Bonato, Aramon; Robert Jacquier, Montpellier, all of France

[73] Assignee: Societe d'Expansion Scientifique "EXPANSIA", Paris, France

[21] Appl. No.: 358,847

[22] Filed: Mar. 17, 1982

[30] Foreign Application Priority Data

Mar. 25, 1981 [GB] United Kingdom ............... 8109392

[51] Int. Cl.³ .............................................. C07F 5/02
[52] U.S. Cl. ...................................................... 549/4
[58] Field of Search .......................................... 549/4

[56] References Cited

PUBLICATIONS

Brown, Organic Synthesis via Borane, Wiley Interscience, New York (1975), pp. 8 & 9.
H. Brown, P. Jadhav and A. Mandal, Asymmetric Synthesis via Chiral Organoborane Reagents, Tetrahedron Report No. 116, pp. 3547–3587.
H. Brown and A. Mandal, Asymmetric Reduction of Representative Ketones with Diisopinocampheylborane of High Optical Purity, J. Org. Chem., vol. 42, No. 18, 1977, pp. 2996–2999.

*Primary Examiner*—Richard Raymond
*Attorney, Agent, or Firm*—Eyre, Mann, Lucas & Just

[57] ABSTRACT

This invention relates to new chiral organoboranes of the general formula

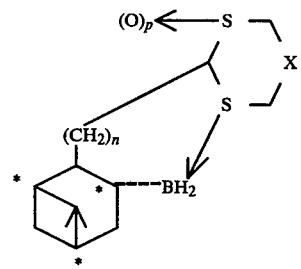

in which X represents a methylene group or a sulphur atom, n and p are 0 or 1, and to a preparation process of these compounds, consisting in reacting a bicyclic substituted di- or tri-thiane with a borane such as $B_2H_6$ or $BH_3$: Lewis base.

1 Claim, No Drawings

BORANE COMPLEXES

DESCRIPTION

The invention relates to optically active borane complexes useful in the asymmetric hydroboration and reduction reactions.

Most of the known chiral hydroboration and reduction agents have the disadvantages of needing to be prepared in situ, of being rather unstable and of not being solid. These disadvantages hinder their commercialisation and handling. The borane complexes according to the invention are solid, stable and can be stored for several months at low temperature.

The invention provides chiral organoboranes of the general formula

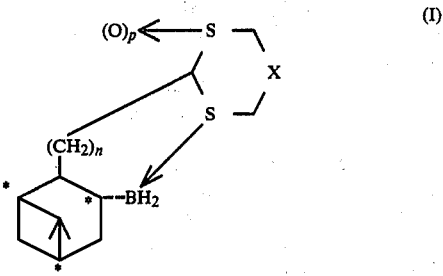
(I)

in which X represents a methylene group or a sulphur atom, n and p are 0 or 1.

These chiral organoboranes are soluble in or miscible with various organic solvents such as methylene dichloride, benzene, diethyl ether, n-pentane, tetrahydrofuran and diglyme. At room temperature, these compounds are solid and their melting points are given. Their asymetric induction power in hydroboration reactions is equivalent to this one of known hydroboration agents, such as mono- and di-isopinocampheylborane or dilongifolyborane.

However, these known compounds present the drawback either of requiring an in situ preparation just before the reaction (mono- and di-isopinocampheylborane) or, for dilongifolyborane, which is a solid dialkyl borane, of being obtained from a compound, the longifolene which is difficult to prepare.

On the contrary, the chiral organoboranes of the invention are optically active monoalkylboranes easily obtainable from commercially available starting materials; they are solid and, consequently, easier to handle.

The compounds according to the invention may be prepared by a method derived from that described by Brown, Organic Synthesis via Borane, Wiley Interscience, New York (1975) pp. 8 and 9, using similar apparatus. More particularly, they may be prepared by reacting for 15' to 2 hours in an inert atmosphere, in an aprotic solvent at a temperature comprised between $-20°$ and $+40°$ C., a bicyclic substituted di- or trithiane of the general formula

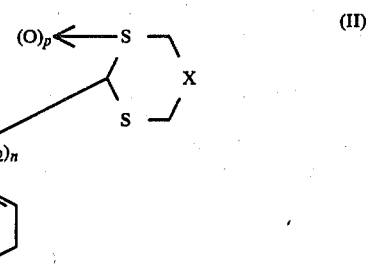
(II)

wherein n, p and X are as defined hereinbefore with a borane such as $B_2H_6$ or $BH_3$:Lewis base.

The compounds wherein $n=1$, $X=CH_2$ or S and $p=0$ or 1 may be obtained starting from commercial $(-)$ myrtenol by halogenation according to the method of G. OSLOFF, F. FARNOW and G. SCHADE, Chem. Ber., 1956, 89, 1549, followed by metal-halogen exchange between the organo-lithium of the 1,3-dithiane or of the 1,3,5-trithiane and the halogen derivative according to D. SEEBACH and E. J. COREY, J. org. Chem., 1975, 40, 231, optionally followed by oxidation using sodium metaperiodate according to O. M. CARLSON and P. M. HELQUIST, J. Org. Chem., 1969, 33, 2596.

The compounds wherein $n=0$, $X=CH_2$ and $p=0$ or 1 may be obtained by condensation of $(-)$ myrtenal and commercial propane 1,3-dithiol according to P. STUTZ and P. A. STADLER, Org. Synth., 1977, 56, 8. The cyclisation product can be oxidised using sodium metaperiodate.

The borane may be obtained according to any of the well known, conventional preparations, or starting from a $BH_3$:Lewis base complex. For example, the borane complex may be obtained by the method described by H. C. BROWN and A. K. MANDAL, Synthesis, 1980, 153, wherein the borane vector is the complex $BH_3$:THF, or by that described by M. ANEZ, G. URIBE, L. MENDOZA and R. CONTRERAS, Synthesis 1981, (3), 214, wherein the borane vector is gaseous diborane.

The invention further provides asymmetric hydroboration and reduction processes in which boranes of the general formula I as hereinbefore defined are used as the hydroboration or reduction agents respectively.

The invention is illustrated by the following Examples:

EXAMPLE 1

2-Myrantyl 1,3-Dithiane Borane ($n=1$, $X=CH_2$, $p=0$)

125 g. (0,429 mole) of 2-myrtényl 1,3-dithiane ($[\alpha]_D^{24} - 8,67$ c=5, benzene) dissolved in 600 ml of anhydrous tetrahydrofuran are poured in a 1 liter reactor under nitrogen circulation. 0.256 mole of diborane ($B_2H_6$) are slowly injected in 1 h 30, in the reaction mixture, cooled at $-10°$ C.

Diborane is obtained by treating 14,25 g (0,375 mole) of sodium borohydride (purity 98%) dissolved in 200 ml of diglyme prealably distillated on aluminium-lithium hydride, dropwise, by 61.5 ml (0.5 mole) of boron trifluoro-etherate, also prealably distillated. The mixture $BH_4N_a - BF_3:(C_2H_5)_2O$ had been warmed at 60° C. for 15 minutes.

After allowing the reaction mixture to reach room temperature, it is stored under nitrogen, with stirring, for 26 hours. The end of the hydroboration reaction is determined by checking the absence of the ethylenic proton by NMR.

After concentration under reduced pressure, there is obtained a white solid compound, m.p. 90° C. (Kofler), with a yield of 93%; ($[\alpha]_D^{24} = -41.79$, c=5, benzene).

The identification of the compound was carried out using the analytical methods given after the Examples.

EXAMPLE 2

2-Myrtanyl 1,3-Dithiane 1-Oxide Borane (n=1, X=CH$_2$, p=1)

The title compound was obtained in 95% yield following the process described in Example 1, but using 2-myrtenyl 1,3-dithiane 1-oxide ($[\alpha]_D^{20} = -8$, c=5.9, benzene) and methylene dichloride as solvent. This is a white solid compound, m.p. 70° ($[\alpha]_D^{21} = +9.12$, c=5, benzene).

The identification of the compound was carried out using the analytical methods given after the Examples.

EXAMPLE 3

2-Myrtanyl 1,3,5-Trithiane Borane (n=1, p=0, X=S)

The title compound was obtained in 94% yield following the process described in Example 1, but using 2-myrtenyl 1,3,5-trithiane ($[\alpha]_D^{21} = -12.16$, c=5, benzene).

This is a white solid compound, m.p. 98°–100° C. (Kofler) $[\alpha]_D^{21} = -4.6$, c=5, benzene). Its identification was carried out using the analytical methods given after the Examples.

EXAMPLE 4

2-[6,6-dimethyl bicyclo[3.1.1]heptyl]1,3-dithiane borane (n=0, p=0, X=CH$_2$)

The title compound was obtained in 96% yield following the process described in Example 1, but using 2-[6,6-dimethyl bicycle[3.1.1]hept-2,3 ene]1,3-dithiane ($[\alpha]_D^{24} = -38.48$, c=4,2, benzene).

This is a white solid compound, m.p. 64°–67° C. (Kofler) $[\alpha]_D^{24} = +14.02$, c=4,1, benzene. Its identification was carried out using the analytical methods given after the Examples.

The stoichiometry and the purity of the complexes obtained in these Examples were determined by methanolysis according to the technique described by J. BERES, A. DODDS, A. J. MORABITO and R. M. ADAMS, Inorg. Chem., 1971, 10, 2072, and by microanalysis.

The structure is confirmed by IR analysis (2% solution in carbon tetrachloride) of the absorption bands between 2360 cm$^{-1}$ and 2400$^{-1}$ characteristic of B-H bonds (H. C. BROWN, E. NEGISHI and J. J. KATZ, J. Amer. Chem. Soc., 1975, 97, 2791) and by NMR H[1], indicating both the disappearance of an ethylenic proton and the presence of —OCH$_3$ of

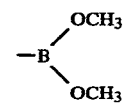

by chemical displacement of methoxy groups following methanolysis at 3.50 ppm (in 1 ml of carbon tetrachloride and 0.45 ml of benzene), according to the method described by A. K. MANDAL and N. M. YOON, J. Organometal. Chem., 1978, 156, 183. The structure is also confirmed by B[11] NMR indicating a thick band between 9 and 10 ppm (internal or external standard, BF$_3$: diethyl ether).

Mass spectroscopy indicates the molecular weight of the compounds with a fragment showing loss of a B—H.

The stability of the complexes obtained has been studied for several months and checked by methanolysis and by IR spectroscopy: the compounds stored under nitrogen atmosphere at low temperature have not shown any alteration. The activity and the interest of the compounds according to the invention have been verified as follows:

(A) In hydroboration reactions by a method deriving from that of A. K. MANDAL and N. M. YOON, J. Organometal. Chem., 1978, 156, 183 for 2-cis-butene; or deriving of that one of P. K. JADHA and H. C. Brown, J. Org. Chem., 1981, 46, 2988, for 2-méthyl 2-butene; or deriving from that one of H. C. BROWN and N. M. YOON, J. Amer. Chem. Soc. 1977, 99, 5514 for 1-methyl cyclohexene.

For instance, optically active organoboranes obtained by the reaction of 2-myrtenyl 1,3-dithiane borane (MDBH$_2$) on those alcenes are oxydised in alcohols by usual methods of oxydation of organoboranes (H. C. BROWN, U.S. Pat. No. 3,254,129). The alcohols thus obtained were purified by gaseous preparative chromatography (Carbowax 400, 20 M), in order to determine their rotation and compare it to the values known in literature (see following table I).

TABLE I

| Olefins | 2-cis-butene | | | 2-methyl 2-butene | | | 1-methyl cyclohexene | |
|---|---|---|---|---|---|---|---|---|
| Alcohols | 2-butanol | | | 3-methyl 2-butanol | | | 2-trans methyl cyclohexanol | |
| $[\alpha]_D$ theori | $[\alpha]_D^{25}$ − 13.5 pure (a) | | | $[\alpha]_D^{27}$ + 4.96 (b) | | | $[\alpha]_D^{20}$ + 43.1 (c) + 42.9 c: 1 CH$_3$OH | |
| (−)IPC$_2$BH | 98.4% | (d) | R | 15% | (d) | S | — | (e) |
| (L-gf)$_2$BH | 78% | (d) | R | 70% | (d) | R | — | |
| (−)IPCBH$_2$ | 25% | (f) | S | 52% | (d) | S | 72% (g) | 1 S 2 S |

TABLE I-continued

| (−)MDBH$_2$ | 27.5% | R | 50% | R | 67.5% | 1 R 2 R |

IPCBH$_2$ = monoisopinocampheylborane
IPC$_2$BH = diisopinocampheylborane
(Lgf)$_2$BH = dilongifolyborane
(a) P. J. LEROUX and H. J. LUCAS, J. Amer. Chem. Soc., 1951, 73, 41.
(b) W. A. SANDERSON and H. S. MOSHER, J. Amer. Chem. Soc., 1966, 88, 4185.
(c) R. BACKSTROM and B. SJOBERG, Arkiv for Kemi, 1967, 26, 549.
(d) P. K. JADHAV and H. C. BROWN, J. Org. Chem., 1981, 46, 2988.
(e) According to H. C. BROWN, N. R. AYANGAR and G. ZWEIFEL, J. Amer. Chem. Soc., 1964, 86, 1071, no reactions of these dialkylboranes on 2-methyl cyclohexene; the alcene is difficult to use for getting an asymmetric induction.
(f) A. K. MANDAL and N. M. YOON, J. Organometal. Chem., 1978, 156, 183.
(g) H. C. Brown and N. M. YOON, J. Amer. Chem. Soc., 1977, 99, 5514.

The asymetric hydroboration of 2-methyl 2-butene by monoisopinocampheylborane (IPCBH$_2$) prepared by the method described in reference (d), above, leads to th obtention of 3-methyl 2-butanol with an optical purity of 9,8% based on maximum rotation $[\alpha]_D^{27}:+4.86$, see reference (b), above, after purification by gaseous preparative chromatography. (Carbowax 400).

The difference in optical purity values 9,8% and 52% (cited by reference (d), above, clearly shows the difficulty of the synthesis of monoisopinocampheylborane IPCBH$_2$ seems to be the only monoalkylborane described in the literature as optically active and non isolated that may be used in asymetric hydroboration reactions.

(B) In asymetric reduction reactions. For instance, that one of acetophenone by 2-[6,6-dimethylbicyclo[3.1.1]heptane]1,3-dithiane borane (PiBH$_2$) has been performed by a method deriving from that one described by H. C. BROWN and A. K. MANDAL, J. Org. Chem., 1977, 42, 2996.

The 1-phenyl ethanol obtained after oxidation of the optically active organoborane, has been purified by gaseous preparative chromatography (Carbowax 20 M). The optical purity of 1-phenyl ethanol is of 16,7% (based on maximum rotation found in literature ($[\alpha]_D^{23} = -45.5$, c: 5, methanol, Handbook of Chemistry and Physics, 1976-7, 57th edition, CRC Press, c 297). The comparative results with two other chiral organoboranes are given in Table II below.

TABLE II

|  | (−) IPC$_2$BH | (−) IPCBH$_2$ | (+)PiBH$_2$ |
|---|---|---|---|
| acetophenone/ 1-phenyl ethanol | 9% (h) | 15% (j) | 16.7% |

(h) H. C. BROWN and A. K. MANDAL, J. Org. Chem., 1977, 42, 2996.
(j) Unpublished work, the results of which have been cited by H. C. BROWN, P. K. JADHAV and A. K. MANDAL, Tetrahedron 1981, 3 (21), 3547.

These new monoalkyl borane asymmetric hydroboration and reduction agents have the advantages of being solid and consequently of an easy handling.

They have an important stability and can be prepared several months before use if stored between 0° and −4° C. They lead to asymmetric compounds and give highly enanthiselective and stereospecific reaction.

We claim:

1. Chiral organoboranes of the formula

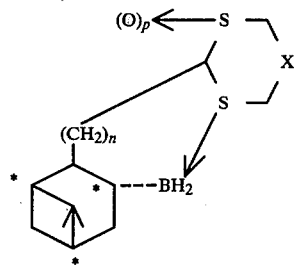

in which X represents a methylene group or a sulphur atom, n and p are 0 or 1.

* * * * *